United States Patent [19]

Chen et al.

[11] Patent Number: 5,684,207

[45] Date of Patent: Nov. 4, 1997

[54] PREPARATION OF METHYL ISOBUTYL KETONE

[75] Inventors: Po-Yu Chen, Tao-Yuan; Shiao-Jung Chu, Hsinchu; Kuo-Ching Wu, King-Men; Wen-Chyi Lin, Hsinchu, all of Taiwan

[73] Assignee: Industrial Technology Research Institute, Hsinchu, Taiwan

[21] Appl. No.: 683,911

[22] Filed: Jul. 19, 1996

Related U.S. Application Data

[63] Continuation of Ser. No. 239,231, May 6, 1994, abandoned.

[51] Int. Cl.⁶ .................................................. C07C 45/45
[52] U.S. Cl. .................................................. 568/396
[58] Field of Search ......................................... 568/390

[56] References Cited

U.S. PATENT DOCUMENTS

| | | | |
|---|---|---|---|
| 3,702,886 | 11/1972 | Argauer | 423/328 |
| 4,270,006 | 5/1981 | Heilen et al. | 568/396 |
| 4,339,606 | 7/1982 | Huang et al. | 568/396 |
| 4,350,835 | 9/1982 | Chester et al. | 585/415 |
| 4,701,562 | 10/1987 | Olson | 568/396 |
| 4,866,210 | 9/1989 | Hoelderich et al. | 568/396 |
| 5,059,724 | 10/1991 | Chen et al. | 568/396 |
| 5,149,881 | 9/1992 | Ushikubo et al. | 568/396 |

FOREIGN PATENT DOCUMENTS

| | | |
|---|---|---|
| 1 535 357 | 8/1968 | France . |
| 30 21 764 | 6/1980 | Germany . |
| 48-16492 | 2/1967 | Japan . |
| 46-2009 | 6/1967 | Japan . |

OTHER PUBLICATIONS

S. Kudo, "Formation of Higher Molecular Weight Ketones from Acetone or Isopropanol," *J. Chem. Soc. Japan Ind., Chem. Sec.* vol. 58, No. 10 (1955) pp. 785–787.

*Primary Examiner*—James H. Reamer
*Attorney, Agent, or Firm*—Darby & Darby

[57] ABSTRACT

A one-step process for selective production of methyl isobutyl ketone includes reacting in the vapor/liquid phase acetone and hydrogen at a temperature of about 100° to 300° C. and a pressure of about 100 to 1000 psig, in the presence of a modified ZSM-5 catalyst having a molar ratio of $SiO_2/Al_2O_3$ from about 20:1 to 680:1, the catalyst being prepared by treating a ZSM-5 zeolite with an organic acid having a pKa of 2 to 5, ion-exchanging or impregnating the ZSM-5 zeolite with a cation selected from the group consisting of palladium cation, platinum cation, copper cation and nickel cation, and activating the resultant catalyst in a reducing atmosphere.

5 Claims, No Drawings

PREPARATION OF METHYL ISOBUTYL KETONE

This is a continuation of application Ser. No. 08/239,231, filed May 6, 1994 now abandoned.

BACKGROUND

MIBK is an important industrial solvent and is mainly used as solvent for nitrocellulose, polyvinyl acetate, acrylic resin, alkyds resin and various adhesives.

MIBK has been produced in a three-stage process in the prior art. The three-stage process comprises aldol condensation of acetone to form diacetone alcohol which is catalyzed by a base, dehydration of that alcohol to mesityl oxide with an acid catalyst, and hydrogenation of that unsaturated ketone to MIBK with nickel or copper chromite catalyst (Kudo, S., "Formation of Higher Molecular Weight Ketones from Acetone or Isopropanol," *J. Chem. Soc.* Japan, Ind, Chem. Sect., 58(1955), 785787; Showa Denkc, "Production of Methyl Isobutyl Ketone from Acetone, " Japanese 46-2009(Jan. 19, 1971); and Minoda, S., et al "Acetone Purification," French 1,535). The disadvantages of the three-stage process are the high cost of the initial manufacturing equipment investment, the necessity of cooling equipment for the condensation of actone to diacetone alcohol, and the problem of acid contamination due to the use of a liquid acid catalyst.

MIBK has also been synthesized from hydrogen and acetone in one step under high pressure in the presence of a palladium-containing cation exchange resin catalyst. The disadvantages of the one-step process include the difficulties of separating the product from by products, the difficulty of obtaining a satisfactory reaction result by selecting an appropriate catalyst, the short lifetime of the catalyst, and the problem of its generation due to the thermal instability of the resin at temperatures above 160° C.

German Offen, 3,021,764 discloses a process for preparing MIBK with a 36% yield using a transition metal complex catalyst, but at a high pressure of 180 atm. It has the disadvantages of high pressure operation, and the difficulties of separating the products form the homogeneous catalyst.

Japan Kokkai 73/16492 describes a process in which MIBK was obtained with a yield of only 13.4% by vapor phase reaction of acetone with hydrogen at 250° C. using a 0.01–2.00% Pd-containing 13X zeolite catalyst.

U.S. Pat. No. 4,339,606 issued to Huang et al discloses a process for the preparation of MIBK using a unmodified zeolite as catalyst. The yield is higher than that of conventional methods, however, is still less than 30% and the lifetime of the catalyst is short.

U.S. Pat. No. 5,059,724 issued Oct. 22, 1991, of common assignee herewith, discloses an one-step process for selective production of MIBK by using ZSM-5 zeolite modified with alkali metal cations as catalyst.

SUMMARY OF THE INVENTION

It is an object of the invention to provide a process for the production of MIBK, which can increase the yield of MIBK and the lifetime of the catalyst.

The process of the invention uses organic acid to modify ZSM-5 series zeolite to produce secondary pores therein, thereby reducing coking; permeates a suitable metal modifier to the zeolites to enhance their catalytic activity by ion exchange or impregnation, and adjusts the basicity and pore size of the zeolite for selective production of MIBK.

Specifically, in accordance with the present invention, the process includes reacting in the vapor/liquid phase acetone and hydrogen at a temperature of about 100° to 300° C. and a pressure of about 100 to 1000 psig, in the presence of a modified ZSM-5 catalyst. The catalyst employed in this process is a crystalline aluminosilicate zeolite having a molar ratio from $SiO_2/Al_2O_3$ of about 20:1 to 680:1 and is prepared by treating a ZSM-5 zeolite with an organic acid having a pKa of 2 to 5, permeating halide, nitrate, sulfate or organic metallic salts of palladium, platinum, copper or nickel to the ZSM-5 zeolite by impregnation or ion-exchange, and activating the resulting catalyst with hydrogen or a mixture of hydrogen and nitrogen at a temperature of 150° to 600° C. for 4 to 24 hours.

According to one aspect of the invention, by using a ZSM-5, a zeolite having shape selectivity and capable of suppressing formation of large molecular substances such as unwanted by-products diisobutyl ketone(DIBK) and light boiling point products formed by direct hydrogenation of acetone, a highly process for forming MIBK is obtained. The yield of MIBK according to the process is as high as 40%.

According to another aspect of the invention, because secondary pores are generated due to the treatment with organic acid, the mass transfer between raw material and products increase, thereby decreasing the deactivation by coking. The impregnated metal ions facilitate homogeneous dispersion of the metal components throughout the zeolite, thereby reducing the formation of polymerized coking material caused by direct hydrogenation of acetone to isopropanol and dehydration. For these reasons the zeolite catalyst has a longer lifetime than that of conventional zeolite catalyst for producing MIBK. The activity of a unmodified zeolite catlyst usually will drop to less than 50% after 4–8 hour reaction, however, the modified zeolite catalysts of the invention can maintain their activity even after continous use for 360 hours.

According to a further aspect of the invention, as the ZSM-5 series zeolite is a highly thermostable catalyst for producing MIBK, the drawbacks of high pressure and thermal instability of resin-supported catalysts associated with conventional processes are avoided.

According to a further aspect of the invention, since a noncorrosive solid catalyst is used, catalyst regeneration is easy; production equipment constructed by special material is not required; and the problems of separating the reaction products from the catalyst is eliminated.

DETAILED DESCRIPTION OF THE INVENTION

The ZSM-5 zeolite used in the invention is a crystalline aluminosilicate zeolite having a molar ratio of $SiO_2/Al_2O_3$ between approximately 20:1 and 680:1. Preferably, the ZSM-5 zeolite should contain such metals as aluminum, titanium, iron, cobalt, boron and have a ratio of silicone to metal between 10 and 100. The ZSM-5 zeolite is modified by soaking in an organic acid having a pKa of 2 to 5 by soaking. Suitable organic acids include citric acid, tartaric acid, acetic acid, formic acid, benzoic acid or maleic acid. The purpose of the soaking treatment is to provide the zeolite with secondary pores so as to increase the mass transfer of the raw material and the products without destroying the crystalline structure of the zeolite. The zeolite, after the soaking treatment, is formed into cylindrical pellets having a diameter from 0.15 cm to 0.5 cm by adding binders. Suitable binders include alumina, kaolin and silica. The proportion of the binders usually falls between 0 and 40 percent by weight, preferably ranging from 0 to 30 percent by weight based on the total amount of the zeolite.

After being modified with organic acids, the ZSM-5 zeolites are ion-exchanged or impregnated with metal cations, e.g., a water-soluble metal salt solution such as a halide, nitrate, sulfate or organic metallic salts to form metal-impregnated zeolite. The cations include palladium platinum, copper or nickel cations. The amount of the cations should be 0.05 to 5 percent by weight based on the total amount of the zeolites. Generally, the ZSM-5 zeolite is soaked in an impregnating solution overnight, then dried and calcined at 200° to 600° C. with the introduction of air. The catalyst, before use, is activated (reduced) by treating it with hydrogen or a mixture of hydrogen and nitrogen at temperatures ranging from 150° to 600° C. for 4 to 24 hours. If a mixture of hydrogen and nitrogen is used, the mixing ratio of $H_2$ to $N_2$ should be in the range of 1:0 to 1:10.

In the instant MIBK synthesis, acetone may be pumped or mixed with hydrogen, preheated and then introduced into a fixed-bed reactor and brought into contact with the catalyst at a temperature of about 100° to 300° C., preferably about 130° to 180° C., and a pressure of at 100 to 1000 psig, preferably 200 to 600 psig. Unreacted acetone, after separation, can be recycled.

The molar ratio of hydrogen to acetone is about 0.3:1 to 4.0:1, and the weight hourly space velocity (WHSV) is 1 to 8 $hr^{-1}$, preferably 1 to 6 $hr^{-1}$.

The examples which follow illustrate the process according to the invention without implying any limitation. In these examples, acetone is pumped and mixed with hydrogen in a pipeline, preheated and then introduced into a ⅜" stainless tube cylindrical reactor and brought into contact with the catalyst at a temperature of 100° to 300° C. The molar ratio of hydrogen to acetone is 0.3:1 to 4:1, the WHSV is 1 to 8 $hr^{-1}$. After the reaction, the reactor effluent is cooled and collected by condensation at the reactor bottom. The collected liquid products are then subjected to gas chromatography by using a HP 5840 A column packed with 10% Carbowax, 2% Benton 34 and 2% KOH on Chromosorb. The column temperature is initially 60° C., and then raised to 130° C. with a rising rate of 1° C./minute after 13 minutes. The injection temperature is 250° C. Nitrogen gas is used as carrier gas and the flow rate thereof is controlled at 10 ml/min. Acetone conversion and MIBK selectivity are calculated respectively using the following equations.

$$\text{conversion (mole \%)} = \frac{\text{molar content of acetone in the feed} - \text{molar content of acetone in the product}}{\text{molar content of acetone in the feed}} \times 100\%$$

$$\text{product selectivity (mole \%)} = \frac{\text{molar content of product} \times \text{stoichiometric ratio}}{\text{molar content of acetone in the feed} - \text{molar content of acetone in the product}} \times 100\%$$

Example 1

Aluminum sulfate(20 g) in an aqueous solution was added to an aqueous solution of water glass (180 g) and tetrapropylammonium bromide (3 g) to provide a silica to alumina molar ratio of 30. The basicity of the resulting solution was adjusted by adding sulfuric acid. The solution was then placed in a 2 liter autoclave, crystallized therein at 160° to 180° C. for 1 day and the formed NaH ZSM-5 zeolite filtered, washed, dried and calcined at 550° C. for 12 hours.

To form the HZSM-5 zeolite, the NaH ZSM-5 zeolite was ion exhanged with $H^+$ ions by treating it with 0.1 M aqueous ammonium nitrate at 80° C. The HZSM-5 zeolite was then extruded into 0.15 cm×0.5 cm pellets, and then calcined at 550° C. for 12 hours.

Pd/HZSM-5 zeolites were obtained by soaking HZSM-5 zeolite(5 g) with an aqueous solution (250 ml) of acetic acid (5 g) for 24 hours, filtering and washing, resoaking with an impregnating (500 ml) solution prepared from 0.4169 g of palladium chloride, 2,4 ml of ammonia water and an appropriate amount of water, filtering, washing and drying at 110° C.

Each of the prepared Pd/HZSM-5 zeolite catalysts was then pulverized into particles of 12 to 20 mesh. 3 g of the particles were disposed in a ⅜" stainless tube cylindrical reactor as a fixed bed, and treated (reduced) with 20 ml of mixed gas of nitrogen and hydrogen at 250° C. for 4 hours. The temperature was then reduced to the reaction temperature of 160° C., acetone was pumped in, mixed with hydrogen, preheated and thereafter brought into contact with the catalyst. The reactor effluent was cooled and collected by condensation at the reactor bottom. The collected liquid products were analyzed by gas chromatography. The results are summarized in Table 1.

Example 2

The same procedures as Example 1 were repeated except that 50 ml of aqueous solution of citric acid (5 g) was used in place of aqueous solution of acetic acid. The results are also summarized in Table 1.

Comparative Example 1

The same procedures as Example 1 were repeated except that 200 ml of 0.5 N hydrochloric acid solution was used in place of aqueous solution of acetic acid. The results are also summarized in Table 1.

Comparative Example 2

Commericalized NaH ZSM-5 zeolite (60 g) with a silica to alumina ratio of 15 was ion exhanged with $H^+$ ions by treating with 0.1 M aqueous ammonium nitrate at 80° C. to form $NH_4$ ZSM-5, washing, drying and extruding into 0.15 cm×0.5 cm pellets, then calcining at 550° C. for 10 hours to form HZSM-5.

Pd/HZSM-5 zeolites were obtained by soaking HZSM-5 zeolite (50 g) with an impregnating (500 ml) solution prepared from 0.4169 g of palladium chloride, 2.4 ml of ammonia water and an appropriate amount of water for 24 hours, filtering, washing, and drying at 110° C.

The same catalytic reaction as in Example 1 was conducted and the products were analyzed by gas chromatography. The results are also listed in Table 1.

TABLE 1

| No. | Acetone Conversion (%) | Product Selectivity (%) | | | |
|---|---|---|---|---|---|
| | | MIBK | Isopropanol | DIBK | Others |
| Example | | | | | |
| 1 | 41.24 | 90.98 | 0.94 | 2.09 | 5.09 |
| 2 | 40.44 | 90.17 | 1.65 | 1.03 | 7.15 |
| Comp. Example | | | | | |
| 1 | 23.31 | 81.01 | 0.28 | 1.56 | 17.15 |
| 2 | 52.24 | 61.12 | 12.83 | 1.88 | 24.17 |

Examples 3 to 5

Aluminum sulfate (2.3–13 g) in aqueous solution was added to an aqueous solution of water glass (180 g) and tetrapropylammonium bromide (3 g). The basicity of the resulting solution was adjusted by adding 1 M sulfuric acid. The solution was then placed in a 2 liter autoclave, crystallized therein at 160° to 180° C. for 1 day, filtered, washed, dried and calcined at 550° C. for 12 hours to form NaH ZSM-5 zeolite having a silica to alumina ratio of 15-300.

To form HZSM-5 zeolite, the NaH ZSM-5 zeolite was ion exhanged with $H^+$ ions by treating with 0.1 M aqueous ammonium nitrate at 80° C., extruded into 0.15 cm×0.5 cm pellets, and calcined at 550° C. for 12 hours.

Pd/HZSM-5 zeolites were obtained by soaking HZSM-5 zeolite(50 g) with an aqueous solution (250 ml) of benzoic acid(10.2 g) for 24 hours, filtering and washing, followed by resoaking with an impregnating(500 ml) solution prepared from 0.4169 g of palladium chloride, 2,4 ml of ammonia water and an appropriate amount of water, and filtering, washing, drying at 110° C.

The same catalytic reaction as in Example 1 was conducted and the products were analyzed by gas chromatography. The results are listed in Table 2.

TABLE 2

| Example No. | $SiO_2$ $Al_2O_3$ | Acetone Conversion (%) | Product Selectivity | | | |
|---|---|---|---|---|---|---|
| | | | MIBK | (%) Iso-propanol | DIBK | Others |
| 3 | 30 | 59.1 | 91.5 | 0.2 | 2.4 | 5.9 |
| 4 | 60 | 57.0 | 90.9 | 0.5 | 3.0 | 5.6 |
| 5 | 100 | 55.1 | 89.2 | 0.3 | 4.3 | 6.2 |

Examples 6-8

2.4 ml of 35% ammonia water was diluted with 150 ml of water, palladium chloride(0.887 g) was added and the solution was diluted with water to 500 ml. HSZM-5 zeolites (50 g) of Example 1 were then ion exchanged respectively with 23.5 ml, 235 ml and 2350 ml of the above $PdCl_2$ diluted solutions to obtain Pd/HZSM-5 catalysts containing 0.05 wt %, 0.5 wt % and 5 wt % Pd. The organic acid used in these examples was tartaric acid.

The same catalytic reaction as in Example 1 was conducted and the products were analyzed by gas chromatography. The results are listed in Table 3.

TABLE 3

| Example No. | Pd Content (wt %) | Acetone Conversion (%) | Product Selectivity (%) | | | |
|---|---|---|---|---|---|---|
| | | | MIBK | Isopropanol | DIBK | Others |
| 6 | 0.05 | 4.91 | 89.2 | 0.5 | 3.2 | 7.1 |
| 7 | 0.5 | 51.4 | 91.09 | 1.5 | 2.4 | 5.0 |
| 8 | 5 | 45.6 | 87.5 | 2.4 | 1.3 | 8.8 |

Examples 9-13

The same catalytic reaction as in Example 1 was conducted except that a Pd/HZSM-5 catalyst containing 0.5 wt % of Pd prepared in Example 7 was used and the reaction temperature was changed to that listed in Table 4 below. The products were analyzed by gas chromatography and the results are listed in Table 4.

TABLE 4

| Example No. | Reaction Temperature (°C.) | Acetone Conversion (%) | Product Selectivity (%) | | | |
|---|---|---|---|---|---|---|
| | | | MIBK | Isopropanol | DIBK | Others |
| 9 | 125 | 40.2 | 82.6 | 0 | 1.0 | 16.4 |
| 10 | 135 | 49.3 | 84.7 | 0.2 | 1.2 | 13.9 |
| 11 | 145 | 63.2 | 92.0 | 1.3 | 2.5 | 4.2 |
| 12 | 150 | 68.3 | 87.2 | 0.6 | 3.2 | 9.0 |
| 13 | 160 | 72.0 | 87.2 | 0.2 | 3.1 | 8.9 |

Examples 14-17

The same catalytic reaction as in Example 1 was conducted except that a Pd/HZSM-5 catalyst containing 0.5 wt % of Pd prepared in Example 7 was used and the WHSV of acetone was changed to that listed in Table 5 below. The products were analyzed by gas chromatography and the results are listed in Table 5.

TABLE 5

| Example No. | WHSV of Acetone ($hr^{-1}$) | Acetone Conversion (%) | Product Selectivity (%) | | | |
|---|---|---|---|---|---|---|
| | | | MIBK | Isopropanol | DIBK | Others |
| 14 | 0.6 | 71.8 | 94.0 | 1.3 | 3.8 | 0.9 |
| 15 | 2 | 68.3 | 92.2 | 1.0 | 1.8 | 5.0 |
| 16 | 5 | 45.4 | 94.0 | 0.4 | 1.4 | 4.2 |
| 17 | 6.5 | 45.1 | 92.0 | 0.5 | 1.3 | 6.2 |

Examples 18-20

The same catalytic reaction as in Example 1 was conducted except that a Pd/HZSM-5 catalyst containing 0.5 wt % of Pd prepared in Example 7 was used and the molar ratio of hydrogen to acetone was changed to that listed in Table 6 below. The products were analyzed by gas chromatography and the results are listed in Table 6.

TABLE 6

| Example No. | Moles to Hydrogen to Acetone | Acetone Conversion (%) | Product Selectivity (%) | | | |
|---|---|---|---|---|---|---|
| | | | MIBK | Isopropanol | DIBK | Others |
| 18 | 1 | 58.0 | 90.6 | 1.3 | 1.5 | 6.6 |
| 19 | 2 | 60.0 | 91.6 | 1.4 | 1.2 | 5.8 |
| 20 | 2.5 | 58.8 | 91.3 | 1.6 | 0.9 | 6.2 |

What is claimed is:

1. A process for the selective production of methyl isobutyl ketone, which comprises: reacting in the vapor/liquid phase acetone and hydrogen at a temperature of about 130° to 180° C. and a pressure of about 100 to 1000 psig, in the presence of a ZSM-5 zeolite having a molar ratio of $SiO_2/Al_2O_3$ from about 20:1 to 680:1, wherein said catalyst is prepared by soaking a ZSM-5 zeolite with an organic acid having a pKa of 2 to 5, wherein said organic acid is selected from the group consisting of citric acid, tartaric acid, acetic acid, formic acid, benzoic acid or maleic acid, so as to form secondary pores, ion-exchanging or impregnating the soaked ZSM-5 zeolite with a palladium, platinum, copper or nickel cation, and activating the resulting catalyst with hydrogen or a mixture of hydrogen and nitrogen at a temperature of 150° to 600° C. for 4 to 24 hours.

2. The process of claim 1, wherein a halide, nitrate, sulfate or organic metallic salt of said cations is used and the amount of the cation is 0.05 to 5% by weight, based on said ZSM-5 zeolite.

3. The process of claim 2, wherein palladium chloride is added to said ZSM-5 zeolite by impregnation.

4. The process of claim 1, wherein, prior to activating, the resulting catalyst is calcined at a temperature of 200° to 600° C. with the introduction of air.

5. The process of claim 1, wherein the reaction is conducted at a hydrogen-to-acetone molar ratio of 0.3 to 4.

* * * * *